(12) United States Patent
Huang

(10) Patent No.: US 10,034,626 B2
(45) Date of Patent: *Jul. 31, 2018

(54) LACTATE MEASURING DEVICE AND METHOD FOR TRAINING ADJUSTMENT IN SPORTS

(71) Applicants: Micro Nipple Technology Co., Ltd., Taipei (TW); National Taipei University of Technology, Taipei (TW)

(72) Inventor: Juang-Tang Huang, Taipei (TW)

(73) Assignee: Micro Nipple Technology Co., Ltd.

( * ) Notice: Subject to any disclaimer, the term of this patent is extended or adjusted under 35 U.S.C. 154(b) by 850 days.

This patent is subject to a terminal disclaimer.

(21) Appl. No.: 14/483,146

(22) Filed: Sep. 10, 2014

(65) Prior Publication Data

US 2015/0208970 A1 Jul. 30, 2015

(30) Foreign Application Priority Data

Jan. 28, 2014 (TW) .............................. 103103313 A

(51) Int. Cl.
*A61B 5/05* (2006.01)
*A61B 5/1486* (2006.01)
*A61B 5/00* (2006.01)
*A61B 5/145* (2006.01)

(52) U.S. Cl.
CPC ...... *A61B 5/14865* (2013.01); *A61B 5/14514* (2013.01); *A61B 5/4866* (2013.01); *A61B 5/685* (2013.01)

(58) Field of Classification Search
CPC .... A61B 5/685; A61B 5/1473; A61B 5/14532
See application file for complete search history.

(56) References Cited

U.S. PATENT DOCUMENTS

| | | | |
|---|---|---|---|
| 6,176,241 B1* | 1/2001 | Blau | A61B 5/222 128/898 |
| 2002/0082543 A1* | 6/2002 | Park | A61B 5/1411 604/21 |
| 2009/0308742 A1* | 12/2009 | Paranjape | A61B 5/0537 204/403.1 |
| 2010/0305473 A1* | 12/2010 | Yuzhakov | A61M 37/0015 600/575 |
| 2015/0208984 A1* | 7/2015 | Huang | A61B 5/685 600/393 |
| 2015/0208985 A1* | 7/2015 | Huang | A61B 5/150282 600/348 |

\* cited by examiner

*Primary Examiner* — Christian Jang
(74) *Attorney, Agent, or Firm* — Parker Ibrahim & Berg LLP; Stephen D. LeBarron

(57) ABSTRACT

The invention relates to a method for training adjustment in sports. The method may measure lactate concentrations in the body of a person by a lactate measuring device comprising a transdermal microneedles sensor. The method for training adjustment in sports includes steps of: measuring a lactate concentration value in the body of a user by the transdermal microneedles sensor; comparing the lactate concentration value with a predetermined value; and informing the user to reduce exercise intensity if the lactate concentration value is higher than the predetermined value, otherwise informing the user to increase exercise intensity if the lactate concentration value is lower than the predetermined value. The invention also relates to a lactate measuring device.

19 Claims, 12 Drawing Sheets

LACTATE MEASURING DEVICE AND METHOD FOR TRAINING ADJUSTMENT IN SPORTS

BACKGROUND OF THE INVENTION

Field of the Invention

The invention relates to a method for training adjustment in sports, particularly a method for training adjustment in sports based on measuring lactate concentrations in the body of a person by a lactate measuring device.

Description of the Related Art

To generate muscle power, a human or other muscle primarily uses carbohydrates as a source of energy. There are two ways, aerobic metabolism and anaerobic metabolism, for carbohydrates to produce energy. As carbohydrates decomposed in anaerobic conditions, the carbohydrates will not only produce energy, but also produce lactate. When exercise intensity is low, muscle generates energy predominantly in the aerobic metabolism and only a small portion in anaerobic metabolism, thus the speed of the lactate production is not high and can be metabolized easily by the human body, so the lactate does not accumulate in the human body and blood. The greater the exercise intensity, the greater the use of the anaerobic metabolism and the higher the speed of the lactate production. The speed of the lactate elimination cannot catch up the speed of the lactate production, and thus the lactate started to accumulate in the human body. At the exercise intensity, the lactate level in the human body between aerobic metabolism and anaerobic metabolism is referred to "lactate threshold." At the lactate threshold between aerobic metabolism and anaerobic metabolism, the lactate level in the human body remains in balance. If the lactate threshold and the associated heart rate of an athlete are known, the athlete can optimize his training according to this.

Lactate is the most important biomarkers in organism oxygenation, and thus the lactate is extremely important in the application of sport and health care. The lactate concentration provides information on anaerobic threshold. This information is very important to develop endurance sports training program. Currently, the development of lactate measuring devices is driven from the commercial interests in sports, fitness, dairy and defence industries.

The normal blood lactate concentration of a human is in the range of 0.5-2 mM in a static resting. However, when a human does a strenuous exercise with the metabolism in the muscle passing into the anaerobic threshold or a human is injured to trigger a hemorrhagic shock, oxygen supplied by cells becomes limited and lactate will increase rapidly. Lactate measurement can help identify the fatigue reaction of athletes and sports lovers and particularly important for soldiers and provides a personalized training process for athletes. Lactate measurement is connected with clinical significance of many intensive care cases, for example, lactateosis, especially in a state of shock.

There are some exercise physiologists proposed the change of blood lactate during exercise and after exercise is in relation to the balance among lactate generation rate of skeletal muscles, the rate of lactate entering the blood and the metabolism rate of lactate in the blood. The blood lactate concentration relates to exercise intensity, lasting time and the metabolism function of tissues and organs. During exercise and after exercise, the physiologic data and the influence of the human body can be obtained by continuously determining blood lactate value. Determination of blood lactate value can be used in training adjustment in sports. In order to provide a perfect training course and plan, a coach has to figure out optimum exercise intensity and demand for an athlete. It was reported in exercise physiological journals that blood lactate value in resting is about 1.0 mM used as a judge basis to exercise intensity, and blood lactate value is about 4.0 mM used as a judge basis to the threshold of the anaerobic metabolism. Another exercise physiological journal disclosed that the blood lactate value may reach about 30 µM/g when a human does a strenuous exercise, and the muscle stressed and hardly to perform exercise when lactate value reaches to 20-25 µM/g in the muscle.

There is an exercise physiological journal disclosed that lactate production in sport is mainly connected with the intensity of exercise loading, portion of muscle involved to exercise and the time during exercise. In addition, lactate concentration is connected with the percentages of aerobic metabolism and anaerobic metabolism in sport. To generate muscle power, a human or other muscle requires energy that must be supplied by the organism. There are three types of energy supply system including phosphagen system, glycolytic system and aerobic system. As energy is supplied by the phosphagen system, blood lactate concentration is low, typically less than 4 mM. As energy is supplied by the glycolytic system, blood lactate concentration may reach to 15 mM. As energy is supplied by the aerobic system, blood lactate concentration is about 4 mM. The change of blood lactate during exercise depends on the energy supply system. Therefore, the accumulation of blood lactate is obviously different with the training intensity. The accumulation of blood lactate has two meanings: one is to generate a lot of energy providing for muscle contraction, for the glycolytic function is accelerated. Another means that acidic level in the muscle is increased, and the energy is supplied predominantly by the anaerobic glycolytic function as a result of the function of aerobic metabolism is not enough. There are some exercise physiologists proposed that the accumulation of blood lactate can be used as a physiological parameter for determining exercise loading of athletes in a stable condition.

The common cause of the accumulation of blood lactate is oxygen deficiency. The lactate concentration is conventionally determined with a lactate test strip which effects a blood analysis of blood samples that are extracted from the athlete at different stresses outside of the laboratory. However, the result has less help for predicting the dynamic change of lactate concentration and establishing a precise concentration again. In fact, the blood sampling is inconvenient when the exercise is implemented. The result cannot be explained directly.

It is not a practical method to directly implant a lactate measurement device in blood vessel that is connected with a risk of thrombus, and causes the interaction between the lactate measurement device and blood flowing through thereof to result in kinetic change of the blood flowing through the lactate measurement device. In contrast, a transdermal sensor is safe by measuring lactate concentration in tissue fluid. Also, the lactate concentration of tissue fluid can provide more information about local oxygen supply. Therefore, the oxygen deficiency of a portion of tissue can be measured without obtaining average value from the blood analysis.

The lactate value is conventionally determined with a lactate measurement device which effects a blood analysis of blood samples that are extracted from the athlete at different stresses. The known solution is, disadvantageously, an invasive method, especially since blood samples must be extracted from the test person (e.g., an athlete) to be tested. This is, on the one hand, sometimes painful for the athlete. On the other hand, the blood extraction is always connected with a risk of infection, for example, with hepatitis or HIV, for both the test person and for the examiner. To reduce this infection risk, high hygiene standards are in turn necessary that make the method elaborate and expensive.

In addition, a conventional non-invasive method to determine the LBP, designated as a "Conconi test", is increasingly being used in sports medicine. In this method, a test person runs on a 400 m athletic track for a length of 200 m with a predetermined speed, for example 8 km/h. After respectively 200 m, the test person increases the tempo in stages, for example, by respectively 0.5 km/h. At each 200 m mark of the athletic track, the test person notes his current heart rate and calls it out to an attendant after respectively circling the athletic track. The test person runs on the track until he has reached a power limit, meaning he cannot further increase the speed.

For test evaluation, the heart rate is plotted against the associated running speed in a two-dimensional (X-Y) diagram. A characteristic finding hereby results: in the aerobic range, given a comparably low power, the heart rate runs nearly linearly with the running speed. This means that the heart rate increases in the same proportion as the power generated by the test person. This regularity is broken at the threshold to the anaerobic metabolism. In the anaerobic high-power range, the heart rate increases comparatively only slightly with further-increasing power or, respectively, running speed. The function of the heart rate dependent on the running speed thus shows a clear, more or less sharp break at the transition from the aerobic low-power range to the anaerobic high-power range, via which the LBP is determined. The heart rate characteristic for the LBP and the associated running speed can be simply read from the X/Y diagram.

However, the Conconi test is comparably elaborate and can hardly be executed without a trained attendant. Additionally, with the Conconi test the LBP can be determined only comparatively imprecisely, due to the weather dependency and the capability of the test person to precisely control his speed.

In summary, there is a need to provide a low invasive lactate measuring device for transdermal continuously monitoring the lactate concentration in the human body. The lactate measuring device is suitable in sports, working out and military training, particularly athletes and sports lovers to avoid muscle acidic and painful.

SUMMARY OF THE INVENTION

One object of the present invention is to provide a method for training adjustment in sports, with which a transdermal microneedles sensor with pricking through skin to sample tissue fluid for measuring lactate concentration in painless and minimally-invasive way. It can help athletes and sports lovers to adjust exercise intensity and exercise frequency, and complete training in sports effectively that training plan is made in accordance with the comparison between a lactate concentration value and a predetermined value.

In order to achieve the object described above, the present invention provides a method for training adjustment in sports, with which a continuous transdermal microneedles sensor comprising a lactate measuring device with pricking through skin to sample tissue fluid for measuring lactate concentration. The method includes steps of: measuring a lactate concentration value in the body of a user by the transdermal microneedles sensor; comparing the lactate concentration value with a predetermined value; and informing the user to reduce exercise intensity if the lactate concentration value is higher than the predetermined value, otherwise informing the user to increase exercise intensity to get the end of the game without acidic muscle if the lactate concentration value is lower than the predetermined value. Furthermore, an allowable lactate concentration range and an allowable lactate concentration change rate may be effectively adjusted to enhance the grade of athletes by determining the finished distance and the residual distance in a race with global positioning system (GPS) or pedometer. Similarly, the lactate concentration value and the concentration change rate can be used as a valid basis for reference for a participant who plays in a ball game or a variety of team sports if rest needed or ball game can be completed.

Another object of the present invention is to provide a lactate measuring device, with which a continuous transdermal microneedles sensor with pricking through skin to sample tissue fluid for measuring lactate concentration in painless and minimally-invasive way.

In order to achieve the object described above, the present invention provides a lactate measuring device comprising a continuous transdermal microneedles sensor and a comparator for comparing a lactate concentration value from a signal processing unit of the continuous transdermal microneedles sensor and a predetermined value. The operation of lactate measuring device of the present invention is based on lactate sensing enzymes to generate hydrogen peroxide with electrical activity, resulting in producing amps of current on a polarized platinum electrode, depends on inner and outer membrane to perform selectivity and biological compatibility.

The onset of blood lactate accumulation (OBLA) is the exercise intensity corresponding to 4 mM lactate concentration, which represents the maximum working load under steady-state concentration of lactate, and corresponds to the transition from the allowable load to more serious exercise intensity. Various studies have demonstrated the importance of OBLA in running performance, and it has also been considered a sensitive adaptation pointer caused by training, and pointer to a sensitive differential pointer among elite athletes.

The method for training adjustment in sports of the invention adjusts the exercise intensity basically based on lactate threshold (LT), anaerobic threshold, maximal lactate steady state (MLSS) or onset of blood lactate accumulation (OBLA) as a predetermined value. The exercise intensity may be reduced when the lactate concentration value is higher than the predetermined value and the lactate concentration change rate increased. To observe if the lactate concentration change rate is reduced until the lactate concentration value returns to the predetermined value. If the lactate concentration value exceeds the predetermined value, but the athlete still maintains the exercise intensity, and the lactate concentration change rate closes to zero, it means that the athlete is in a good physical at that time, and thus the exercise intensity can be maintained. Furthermore, the exercise intensity can be increased slightly, observing if the lactate concentration change rate is increased continuously or a balance point without changing. Accordingly, in the same predetermined value of lactate concentration, athletes can break through the exercise intensity in the past, such as running, its speed can be accelerated, and such as swimming, its swimming speed can be accelerated, so that race results can be progressive.

In another embodiment, the method of the invention adjusts the exercise intensity based on individual anaerobic threshold (IAT) as a predetermined value. IAT is defined as a running speed that lactate concentration value has an increased amount of 1.5 mM than lactate threshold (LT).

The continuous transdermal microneedle sensor according to the invention includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the peripheral. One of the sheets provides the through hole from which the barbules at the edge of the other sheets go through, and the barbules are disposed separately.

Accordingly, the invention provides a continuous transdermal microneedles sensor with pricking through skin to sample tissue fluid for measuring lactate concentration in painless and minimally-invasive way. Also, the transdermal microneedles sensor can be simple to wear, and accurate to measure the lactate concentration in a human body. It can help athletes and sports lovers to obtain biological parameters more accurately and adjust exercise intensity and exercise frequency to achieve training in sports effectively.

DETAILED DESCRIPTION OF THE INVENTION

Figure 1:
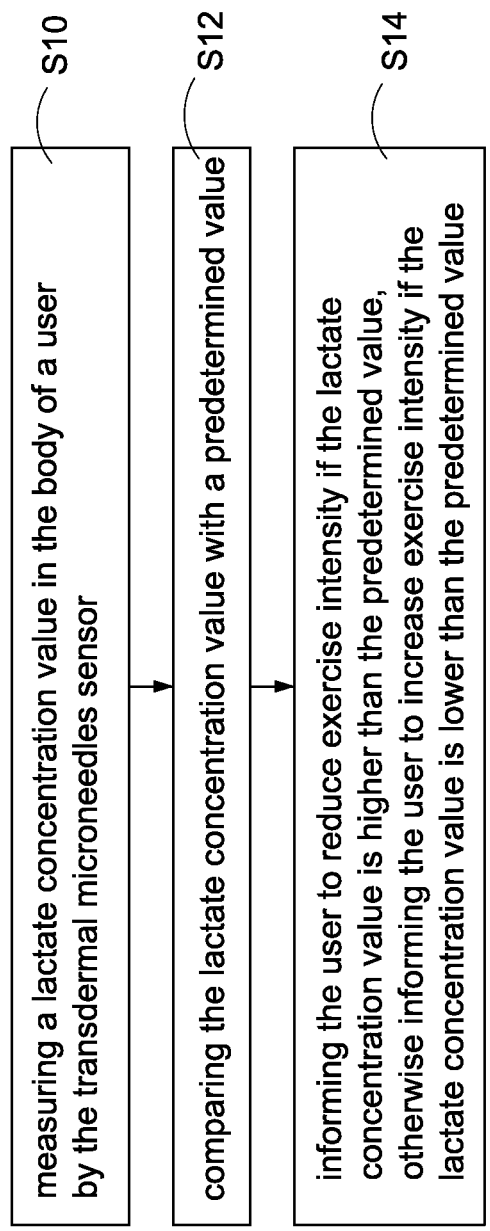
FIG. 1 shows flow chart of steps of the method for training adjustment in sports according to an embodiment of the present invention.

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

Please refer to FIG. 1. FIG. 1 shows flow chart of steps of the method for training adjustment in sports according to an embodiment of the present invention. The method may measure lactate concentrations in the body of a person by a lactate measuring device comprising a transdermal microneedles sensor. The method for training adjustment in sports includes steps of: step S10, measuring a lactate concentration value in the body of a user by the transdermal microneedles sensor; step S12, comparing the lactate concentration value with a predetermined value; and step S14, informing the user to reduce exercise intensity if the lactate concentration value is higher than the predetermined value, otherwise informing the user to increase exercise intensity if the lactate concentration value is lower than the predetermined value. The predetermined value of step S12 is based on lactate threshold (LT), anaerobic threshold, maximal lactate steady state (MLSS), onset of blood lactate accumulation (OBLA) or individual anaerobic threshold (IAT).

In an embodiment of the invention, the lactate measuring device comprises a continuous transdermal microneedles sensor and a comparator (not shown in figures) for comparing a lactate concentration value from a signal processing unit of the continuous transdermal microneedles sensor and a predetermined value.

Figure 2:
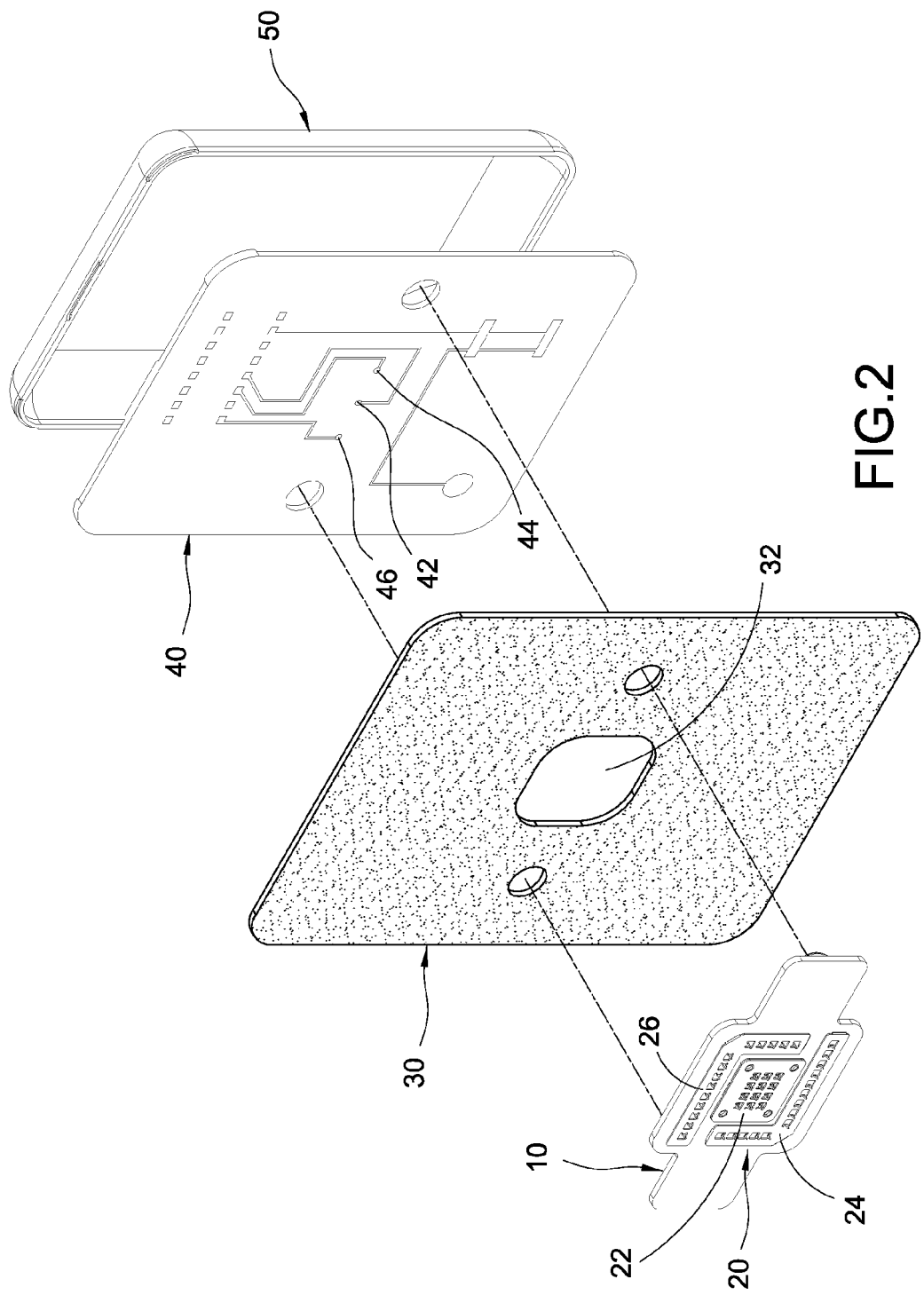
FIG. 2 shows the exploded view of the transdermal microneedles sensor according to an embodiment of the present invention from one viewing direction.
Figure 3:
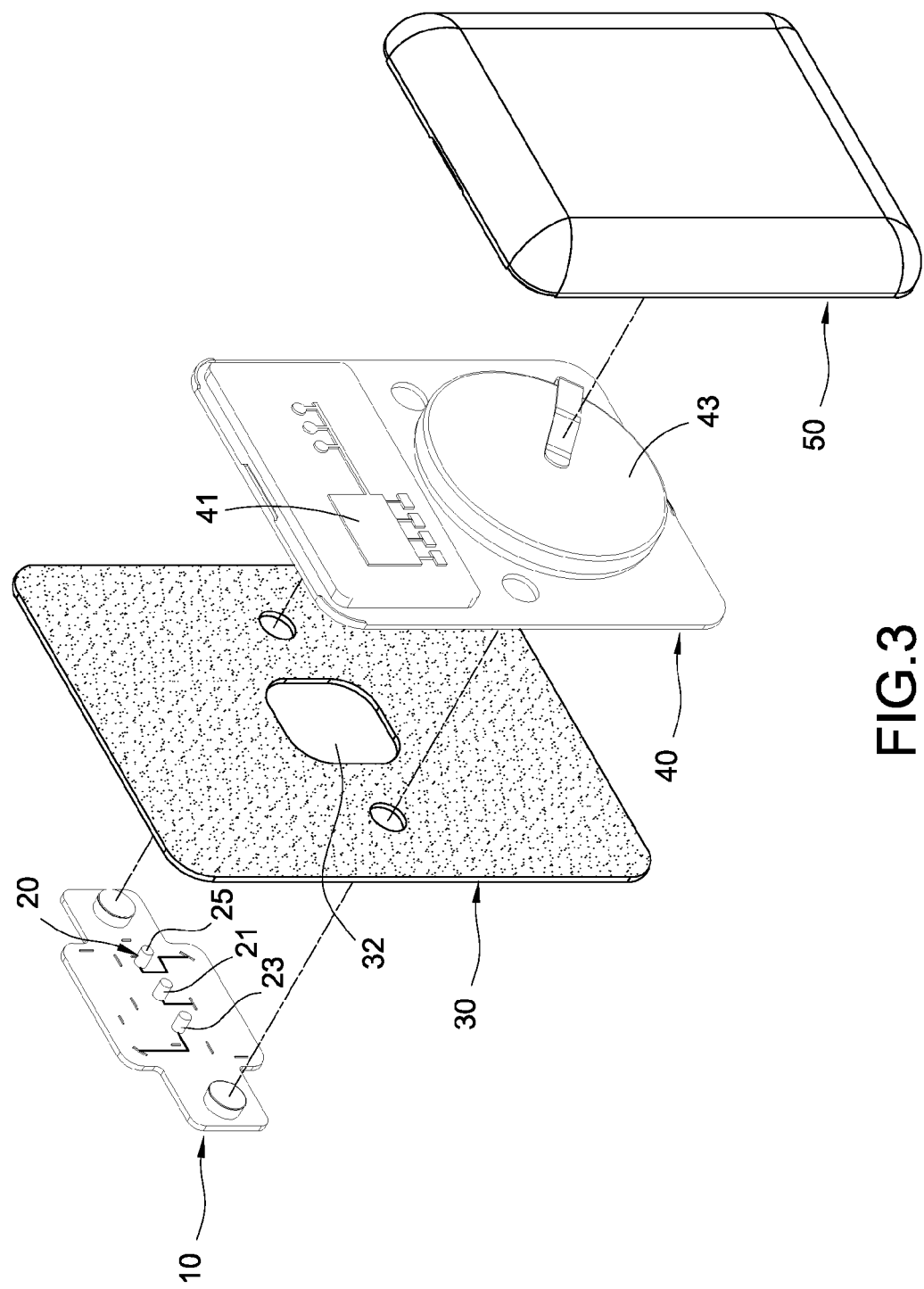
FIG. 3 shows the exploded view of the transdermal microneedles sensor from another viewing direction.

FIG. 2 shows the exploded view of the transdermal microneedles sensor according to an embodiment of the present invention from one viewing direction, and FIG. 3 shows the exploded view of the transdermal microneedles sensor from another viewing direction. The transdermal microneedles sensor of the present invention mainly comprises a substrate 10, a microneedle unit 20, a flexible pad 30, a signal processing unit 41, a power supply unit 43 and a cover 50, where the signal processing unit 41 and the power supply unit 43 are arranged on a circuit board 40.

According to an embodiment of the present invention, the microneedle unit 20 comprises a first microneedle set 22 used as a working electrode, a second microneedle set 24 used as a reference electrode, and a third microneedle set 26 used as a counter electrode, wherein the first microneedle set 22 is coated with SPEES/PES membrane and lactate sensing enzyme. The flexible pad 30 has an opening 32 through which the microneedle unit 20 passes. The microneedle unit 20 further comprises electric conducting posts 21, 23, 25 to respectively and electrically connect to the contacts 42, 44 and 46 on the circuit board 40. The transdermal microneedles sensor of the present invention uses the flexible pad 30 to have tight fit with the user's muscle during operating thereof. When the microneedle unit 20 is inserted to hypodermal tissue of a human, and imposes polarization voltage to the electrodes, the lactate sensing enzyme reacts with lactate in the tissue fluid to produce hydrogen peroxide with electrical activity and produce amps of current on work electrode, wherein the current is proportional to the concentration of lactate.

The signal processing unit 41 electrically connects to the microneedle unit 20 and receives a concentration data of hypodermal target molecules sensed by the microneedle unit 20. The signal processing unit 41 generates a sensing signal manifesting the current physiological condition of user after processing the received concentration data. The power supply unit 43 provides working power to the transdermal microneedles sensor of the present invention.

Figure 4:
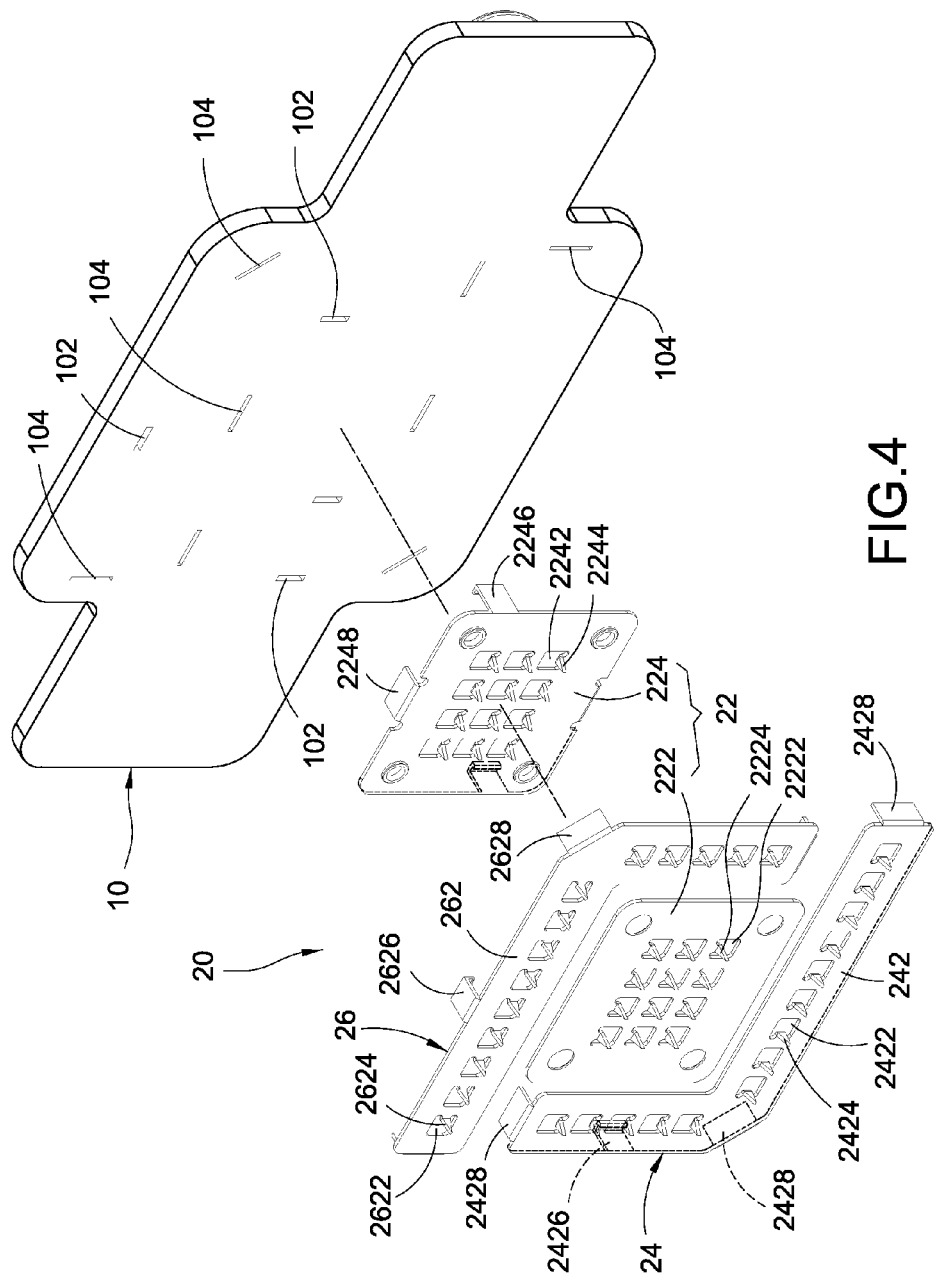
FIG. 4 shows a schematic exploded view of the microneedle unit according to an embodiment of the present invention.

FIG. 4 shows a schematic exploded view of the microneedle unit 20 according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224. The second sheet 224 of the first microneedle set 22 comprises barb 2246 at the peripheral thereof and matched with the aperture 102 defined on the substrate 10. According to another embodiment, the second sheet 224 of the first microneedle set 22 comprises conductive pin 2248 at the peripheral thereof. The conductive pin 2248 can be inserted into a slot 104 defined on the substrate 10 to electrically connect to the conductive post 21.

Similarly, the second microneedle set 24 comprises a first sheet 242. The first sheet 242 has at least one first through hole 2422 defined thereon, and a first barbule 2424 at peripheral of the first through hole 2422. The first sheet 242 of the second microneedle set 24 comprises barb 2426 at the peripheral thereof and matched with the aperture 102 defined on the substrate 10. According to another embodiment, the first sheet 242 of the second microneedle set 24 comprises conductive pin 2428 at the peripheral thereof. The conductive pin 2428 can be inserted into a slot 104 defined on the substrate 10 to electrically connect to the conductive post 23.

Similarly, the third microneedle set 26 also comprises a first sheet 262. The first sheet 262 has at least one first through hole 2622 defined thereon, and a first barbule 2624 at peripheral of the first through hole 2622. The first sheet 262 of the third microneedle set 26 comprises barb 2626 at the peripheral thereof and matched with the aperture 102 defined on the substrate 10. According to another embodiment, the first sheet 262 of the third microneedle set 26 comprises conductive pin 2628 at the peripheral thereof. The conductive pin 2628 can be inserted into a slot 104 defined on the substrate 10 to electrically connect to the conductive post 25.

According to an embodiment of the present invention, the first microneedle set 22, the second microneedle set 24, and the third microneedle set 26 can be made by punching or etching process. The material of the barbules is selected from the group consisting of stainless steel, nickel, nickel alloy, titanium, titanium alloy, carbon nanotube, and silicon. The surface of the barbules is coated with biologically compatible metal. The material of the barbules can also be selected from the group consisting of polycarbonate, polymethacrylic acid, polytetrafluoroethylene, and polyester. The surface of the barbules is also coated with biologically compatible metal. Moreover, the height of the barbules is 300-600 micrometers; the base width of the barbules is 150-450 micrometers. The separation between tips of the barbules is 500-3000 micrometers.

With reference to FIGS. 5 to 8, FIG. 5 is a top view of the microneedle set functioning as working electrode according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224.

Figure 6:
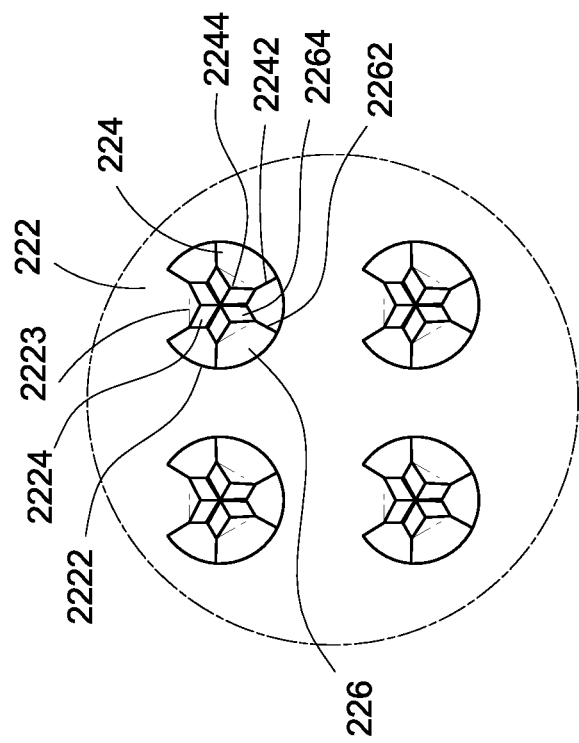
FIG. 6 is a top view of the microneedle set functioning as working electrode according to another embodiment of the present invention.
Figure 5:
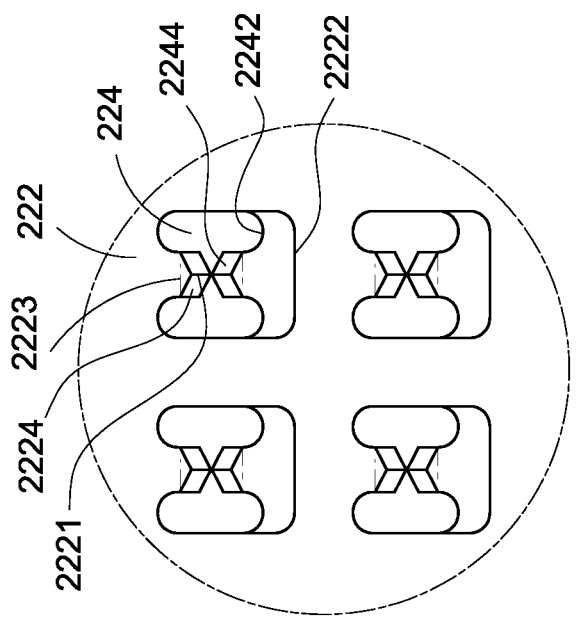
FIG. 5 is a top view of the microneedle set functioning as working electrode according to an embodiment of the present invention.

FIG. 6 is a top view of the microneedle set functioning as working electrode according to another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in right triangular arrangement from top view.

Figure 7:
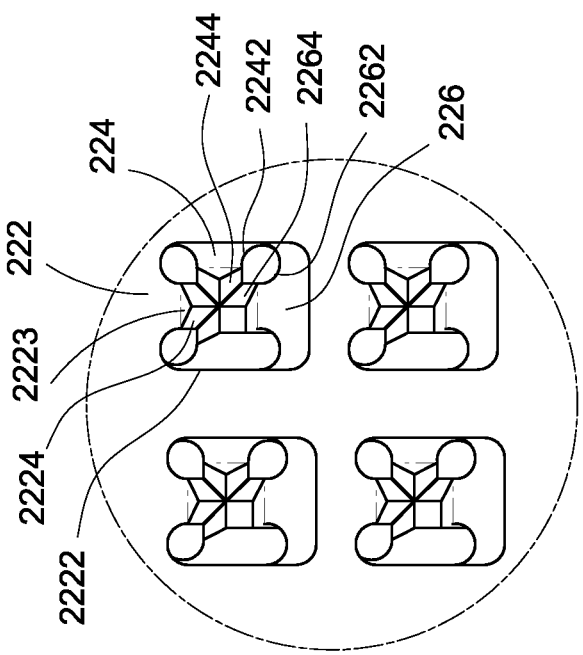
FIG. 7 is a top view of the microneedle set functioning as working electrode according to still another embodiment of the present invention.

FIG. 7 is a top view of the microneedle set functioning as working electrode according to still another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in isosceles triangular arrangement from top view.

Figure 8:
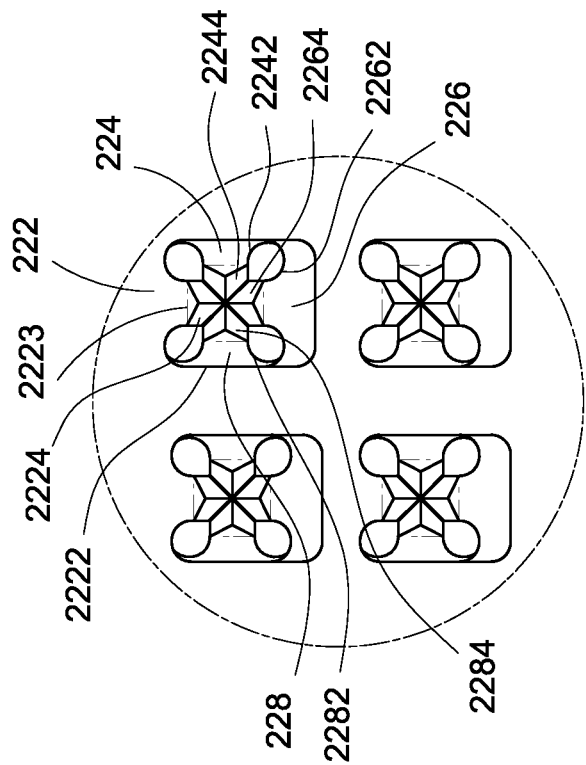
FIG. 8 is a top view of the microneedle set functioning as working electrode according to still another embodiment of the present invention.

FIG. 8 is a top view of the microneedle set functioning as working electrode according to still another embodiment of the present invention. The first microneedle set 22 comprises a first sheet 222, a second sheet 224, a third sheet 226 and a fourth sheet 228 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The fourth sheet 228 has at least one fourth through hole 2282 defined thereon, and a fourth barbule 2284 at peripheral of the fourth through hole 2282. The second barbule 2244, the third barbule 2264 and the fourth barbule 228 penetrates the first through hole 2222 to juxtapose the first barbule 2224, and the tips of the barbules are in rectangular arrangement from top view.

In the embodiments shown in FIGS. 5 to 8, the barbule 2224 of the first microneedle set 22 comprises a tip 2221 and a base 2223. The tips of those barbules, after the sheets are stacked together, are not at the same altitudes. Namely, some barbules pass more through holes than other barbules. Alternatively, the height of the barbules can be such designed, based on the stacked order of sheets, that the tips of those barbules, after the sheets are stacked together, are at the same altitudes.

Figure 9:
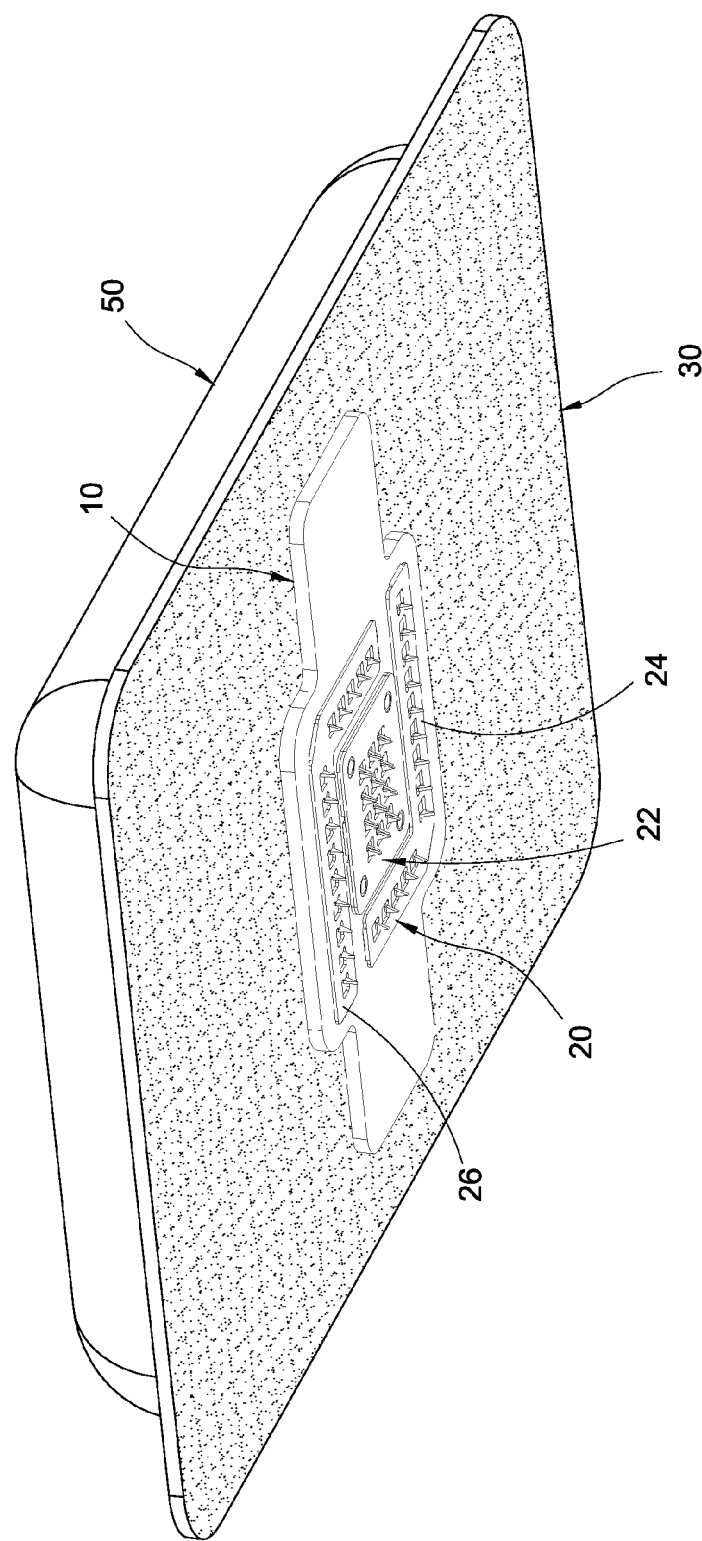
FIG. 9 shows a perspective of an assembled transdermal microneedles sensor according to an embodiment of the present invention.
Figure 10:
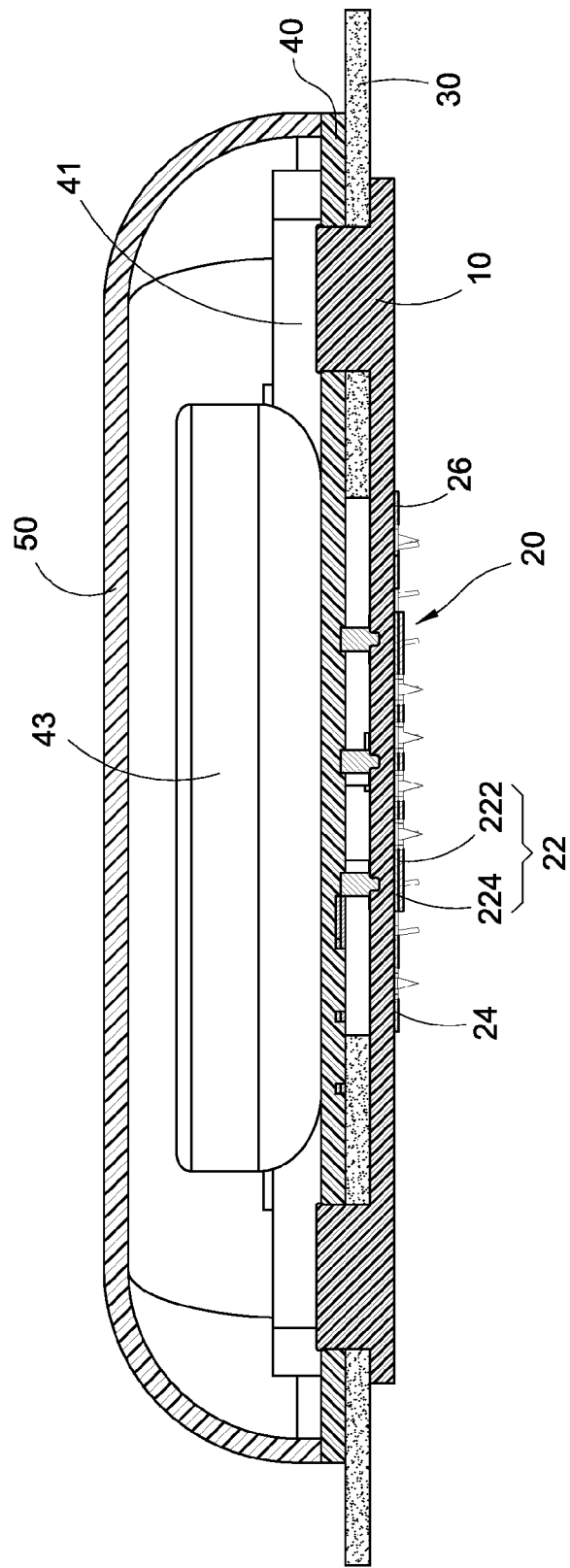
FIG. 10 shows a sectional of an assembled transdermal microneedles sensor according to an embodiment of the present invention.

Next, please refer to FIGS. 9 and 10. FIG. 9 shows a perspective of an assembled transdermal microneedles sensor according to an embodiment of the present invention. FIG. 10 shows a sectional of an assembled transdermal microneedles sensor according to an embodiment of the present invention. In this shown embodiment, the first microneedle set 22 comprises a first sheet 222 and a second sheet 224 stacked with each other. The first sheet 222 and the second sheet 224 can be assembled by punching peripherals thereof. The second microneedle set 24 comprises only a first sheet 242 and the third microneedle set 26 comprises only a first sheet 262. The transdermal microneedles sensor of the present invention uses the flexible pad 30 to have tight fit with the user's muscle during operation thereof.

Figure 11:
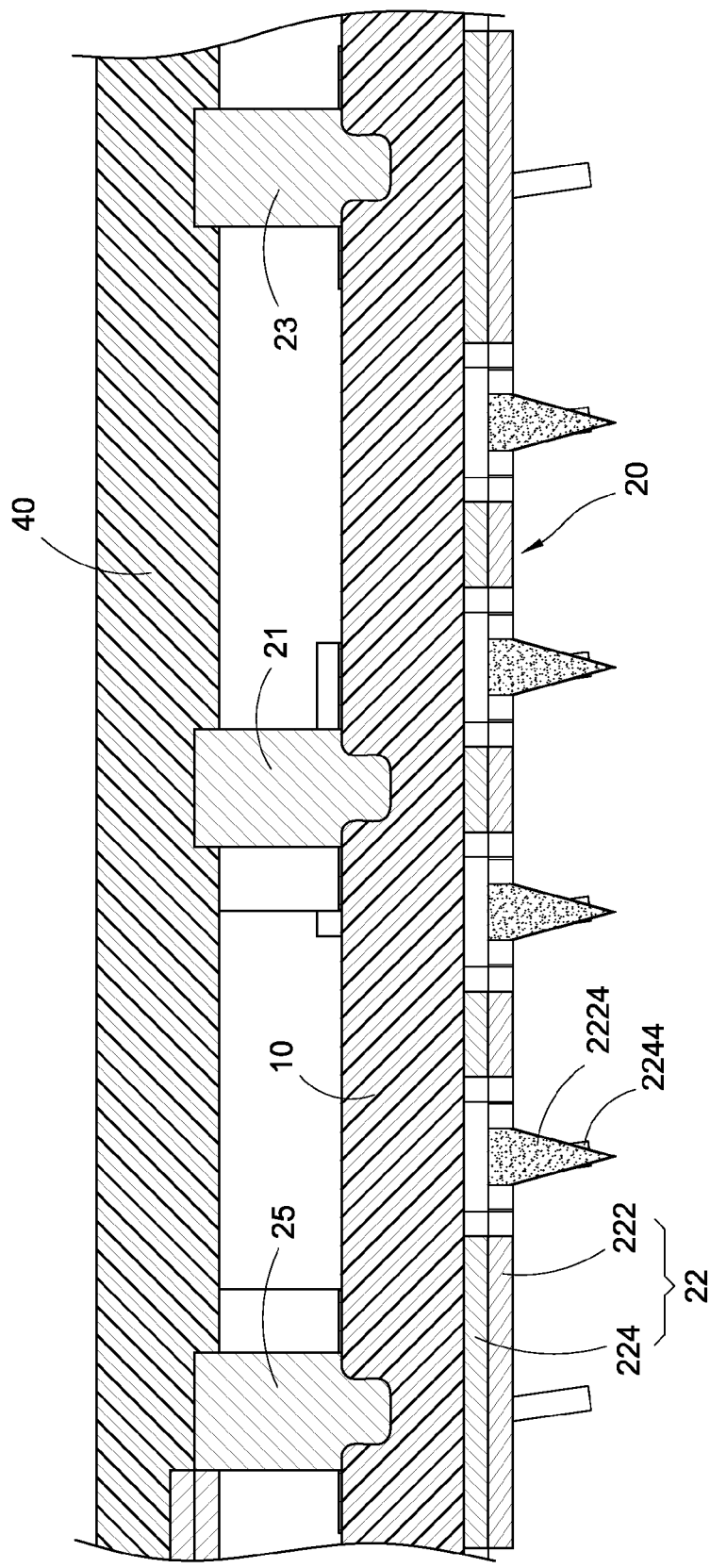
FIG. 11 is a partially sectional view of FIG. 10, where lactate sensing enzyme is coated on the barbules to form a lactate enzyme layer.

FIG. 11 is a partially sectional view of FIG. 10, where lactate sensing enzyme is coated on the barbules to form a lactate enzyme layer. More particularly, the lactate sensing enzyme is coated on the inner faces of the barbules, and anti-irritation medicine (medicine preventing skin from irritation) is coated on outer faces of the barbules. The continuous transdermal microneedles sensor having barbules coated with the lactate sensing enzyme can sense the concentration data of hypodermal lactate and determine the current physiological condition of user with the concentration data.

Figure 12:
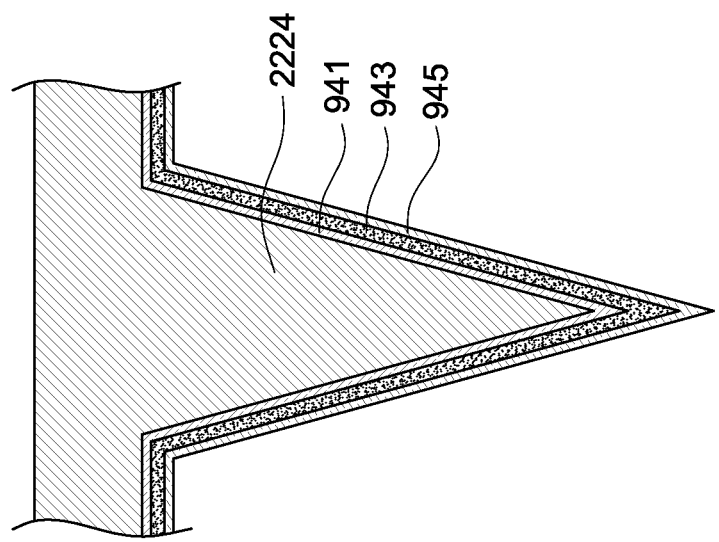
FIG. 12 is a partially enlarged sectional view of the barbule in FIG. 11.

Next, please refer to FIG. 12. FIG. 12 is a partially enlarged sectional view of the barbule in FIG. 11. Since the ammeter electrochemical method is usually less selective, many common interference, most notably ascorbic acid that may present in plasma to interfere the signal. In order to achieve high lactate selectivity, a semi-permeable membrane 941 such as sulfonated polyether ether sulphone/polyether sulfone (SPEES/PES) membrane is formed on the surface of the electrodes, and then a lactate enzyme layer 943 is formed on the semi-permeable membrane 941. SPEES/PES membrane with negative charge allow small neutral molecules to permeate, but does not allow ascorbic acid to permeate. Also, in order to prevent the lactate sensing enzyme and the anti-irritation medicine from environment pollution, a protection layer 945 such as an epoxy-polyurethane (Epoxy-PU) film is formed on the surface of the lactate enzyme layer 943 and the anti-irritation medicine.

Figure 13:
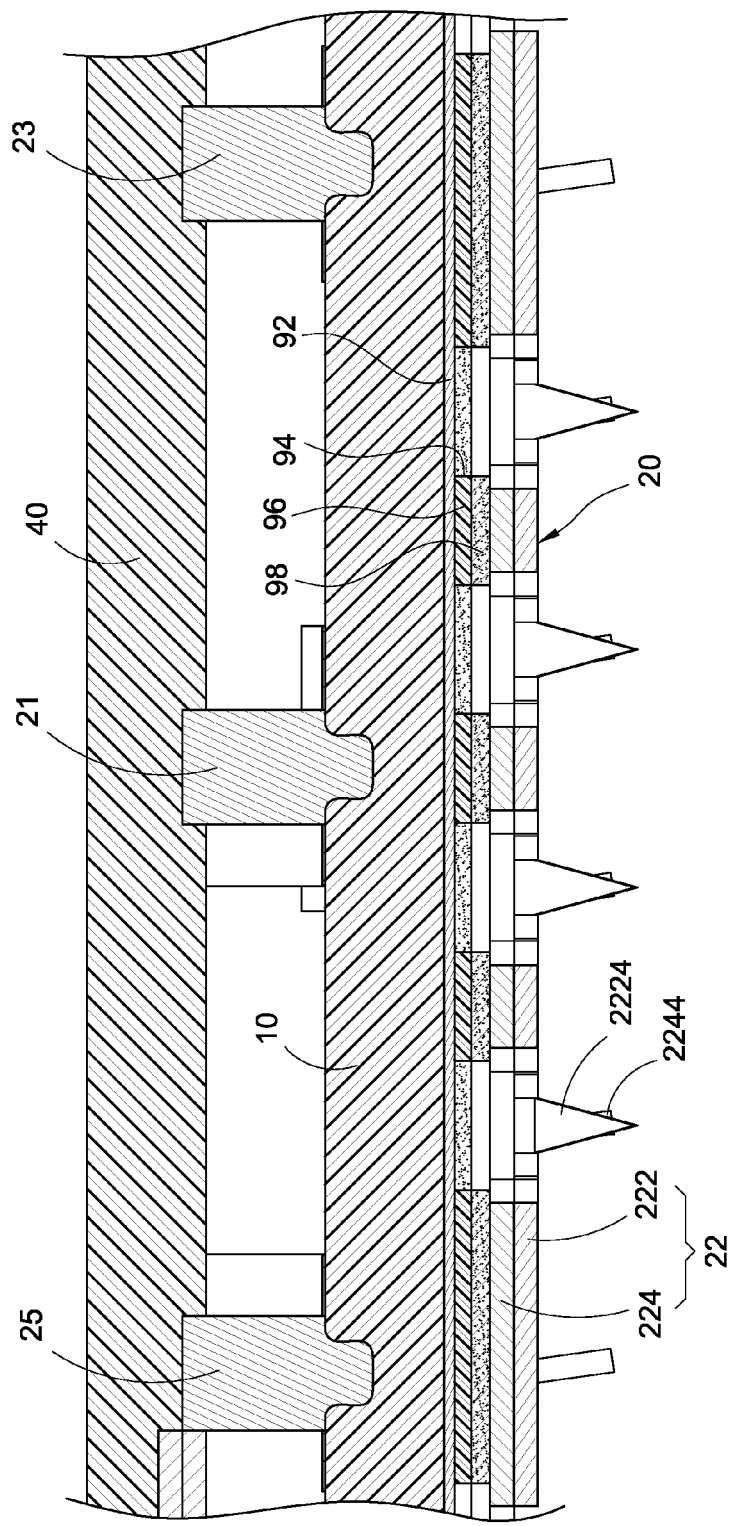
FIG. 13 is a partially sectional view of FIG. 10, where lactate sensing enzyme is coated on a test strip.

FIG. 13 is a partially sectional view of FIG. 10, where sensing polymer is coated on a test strip. The embodiment shown in this figure is different with the embodiment of FIG. 11 in that the first microneedle set 22 in this embodiment is used to withdraw interstitial fluid. Therefore, the sensing polymer is coated on a test strip below the first microneedle set 22 instead of coating on the barbules. In this embodiment, the test strip is arranged between the first microneedle set 22 and the substrate 10. The test strip comprises a conductive layer 92 and a plurality of test areas 94 on the conductive layer 92. The test areas 94 are coated with sensing polymer and aligned with the through holes 2222 of the first microneedle set 22. In this embodiment, the test areas 94 are defined by the resin plate 96. Moreover, the first microneedle set 22 is fixed to the test strip by a binding layer 98.

Figure 14:
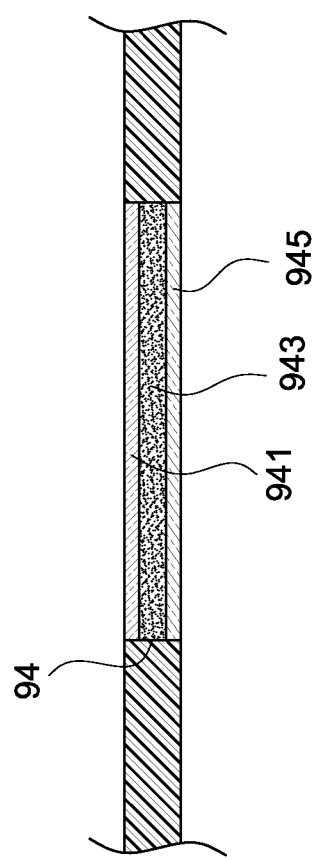
FIG. 14 is a partially enlarged sectional view of the test strip in FIG. 13.

Next, please refer to FIG. 14. FIG. 14 is a partially enlarged sectional view of the test strip in FIG. 13. Similarly, in order to achieve high lactate selectivity, a semi-permeable membrane 941 such as sulfonated polyether ether sulphone/ polyether sulfone (SPEES/PES) membrane is formed on the surface of the electrodes, and then a lactate enzyme layer 943 is formed on the semi-permeable membrane 941. SPEES/PES membrane with negative charge allow small neutral molecules to permeate, but does not allow ascorbic acid to permeate. Also, in order to prevent the lactate sensing enzyme and the anti-irritation medicine from environment pollution, a protection layer 945 such as an epoxy-polyurethane (Epoxy-PU) film is formed on the surface of the lactate enzyme layer 943 and the anti-irritation medicine. Besides lactate oxidase may be used as the lactate sensing enzyme, lactate dehydrogenase, cytochrome b2, lactate monooxygenase and hydrogen peroxidase are suitable as the lactate sensing enzyme.

As the skilled person will appreciate, various changes and modifications can be made to the described embodiments. It is intended to include all such variations, modifications and equivalents which fall within the scope of the invention, as defined in the accompanying claims.

What is claimed is:

1. A method for training adjustment in sports, with which a lactate measuring device comprising a continuous transdermal microneedles sensor is used to measure lactate concentration in a human body, the method including steps of:
   measuring a lactate concentration value in the body of a user by the continuous transdermal microneedles sensor;
   comparing the lactate concentration value with a predetermined value; and
   informing the user to reduce exercise intensity if the lactate concentration value is higher than the predetermined value, and otherwise informing the user to increase exercise intensity if the lactate concentration value is lower than the predetermined value;
   wherein the continuous transdermal microneedles sensor comprises:
      a substrate;
      a microneedle unit comprising at least a first microneedle set used as a working electrode and a second microneedle set used as a reference electrode, each of the microneedle sets comprising at least a microneedle, the first microneedle set comprising at least two sheets, each of the sheets having a through hole defined thereon and a barbule arranged at the peripheral of the through hole, the through hole on one sheet allowing the corresponding barbules of another sheet to pass and the barbules being disposed separately;
      a signal processing unit arranged on the substrate and electrically connecting to the first microneedle set and the second microneedle set; and
      a power supply unit providing working power to the transdermal microneedles sensor.

2. The method for training adjustment in sports in claim 1, wherein the first microneedle set comprises a first sheet and a second sheet stacked with the first sheet, the first sheet having at least one first through hole defined thereon, and a first barbule at peripheral of the first through hole, the second sheet having at least one second through hole defined thereon and a second barbule at peripheral of the second through hole, wherein the second barbule penetrates the first through hole to juxtapose the first barbule at corresponding location.

3. The method for training adjustment in sports in claim 1, wherein the first microneedle set comprises a first sheet, a second sheet and a third sheet stacked with each other, the first sheet having at least one first through hole defined thereon, and a first barbule at peripheral of the first through hole, the second sheet having at least one second through hole defined thereon and a second barbule at peripheral of the second through hole, the third sheet having at least one third through hole defined thereon and a third barbule at peripheral of the third through hole, wherein the second barbule and the third barbule penetrate the first through hole to juxtapose the first barbule, and tips of the barbules are in triangular arrangement.

4. The method for training adjustment in sports in claim 1, wherein the first microneedle set comprises a first sheet, a second sheet, a third sheet and a fourth sheet stacked with each other, the first sheet having at least one first through hole defined thereon, and a first barbule at peripheral of the first through hole, the second sheet having at least one second through hole defined thereon and a second barbule at peripheral of the second through hole, the third sheet having at least one third through hole defined thereon and a third barbule at peripheral of the third through hole, the fourth sheet having at least one fourth through hole defined thereon and a fourth barbule at peripheral of the fourth through hole, wherein the second barbule, the third barbule and the fourth barbule penetrate the first through hole to juxtapose the first barbule, and tips of the barbules are in rectangular arrangement.

5. The method for training adjustment in sports in claim 1, wherein the microneedles of first microneedle set and the second microneedle set are formed by punching or etching.

6. The method for training adjustment in sports in claim 1, wherein each the barbules has lactate sensing enzyme coated on inner surface thereof.

7. The method for training adjustment in sports in claim 1, wherein each the barbules has anti-irritation medicine coated on outer surface thereof.

8. The method for training adjustment in sports in claim 1, wherein the continuous transdermal microneedles sensor further comprises a test strip arranged between the first microneedle set and the substrate, the test strip comprises a conductive layer and a plurality of test areas on the conductive layer, the test areas are coated with sensing polymer and aligned with the through holes of the first microneedle set.

9. The method for training adjustment in sports in claim 6, further comprising a protection layer on the lactate sensing enzyme.

10. The method for training adjustment in sports in claim 7, further comprising a protection layer on the anti-irritation medicine.

11. The method for training adjustment in sports in claim 1, wherein the material of the barbules is selected from the group consisting of stainless steel, nickel, nickel alloy, titanium, titanium alloy, carbon nanotube, and silicon, the surface of the barbules is coated with biologically compatible metal.

12. The method for training adjustment in sports in claim 1, wherein the material of the barbules is resin, the surface of the barbules is coated with biologically compatible metal.

13. The method for training adjustment in sports in claim 1, the predetermined value is lactate threshold (LT), anaerobic threshold, maximal lactate steady state (MLSS) or onset of blood lactate accumulation (OBLA).

14. The method for training adjustment in sports in claim 1, the predetermined value is individual anaerobic threshold (IAT) of a user.

15. A lactate measuring device, comprising:
a substrate;
a microneedle unit comprising at least a first microneedle set used as a working electrode and a second microneedle set used as a reference electrode, each of the microneedle sets comprising at least a microneedle, the first microneedle set comprising at least two sheets, each of the sheets having a through hole defined thereon and a barbule arranged at the peripheral of the through hole, the through hole on one sheet allowing the corresponding barbules of another sheet to pass and the barbules being disposed separately;
a signal processing unit arranged on the substrate and electrically connecting to the first microneedle set and the second microneedle set;
a comparator for comparing a lactate concentration value from the signal processing unit and a predetermined value; and
a power supply unit providing working power to the transdermal microneedles sensor.

16. The lactate measuring device in claim 15, wherein the microneedles of first microneedle set and the second microneedle set are formed by punching or etching.

17. The lactate measuring device in claim 15, wherein each the barbules has lactate sensing enzyme coated on inner surface thereof.

18. The lactate measuring device in claim 15, wherein each the barbules has anti-irritation medicine coated on outer surface thereof.

19. The lactate measuring device in claim 15, further comprising a test strip arranged between the first microneedle set and the substrate, the test strip comprises a conductive layer and a plurality of test areas on the conductive layer, the test areas are coated with sensing polymer and aligned with the through holes of the first microneedle set.

* * * * *